(12) United States Patent
Yanagawa

(10) Patent No.: US 6,197,328 B1
(45) Date of Patent: Mar. 6, 2001

(54) NASALLY ADMINISTRABLE COMPOSITIONS

(75) Inventor: Akira Yanagawa, Yokohama (JP)

(73) Assignee: Dott Research Laboratory, Yokohama (JP)

( * ) Notice: Subject to any disclaimer, the term of this patent is extended or adjusted under 35 U.S.C. 154(b) by 0 days.

(21) Appl. No.: 09/377,905

(22) Filed: Aug. 20, 1999

(51) Int. Cl.$^7$ ............................ A61F 13/00; A61K 38/00; A61K 38/28

(52) U.S. Cl. .................... 424/434; 514/2; 514/3; 514/21; 514/57; 424/489; 424/494; 424/499

(58) Field of Search .................. 514/2, 3, 21, 57, 514/573; 424/434, 489, 689, 499, 494

(56) References Cited

U.S. PATENT DOCUMENTS

| | | | |
|---|---|---|---|
| 5,183,802 | * | 2/1993 | Aliverti et al. .................... 514/2 |
| 5,578,567 | * | 11/1996 | Cardinaux et al. .................... 514/12 |
| 5,603,943 | * | 2/1997 | Yanagawa ............................ 424/434 |
| 5,908,824 | * | 6/1999 | Yanagawa ................................ 514/2 |

\* cited by examiner

*Primary Examiner*—Gollamudi S. Kishore
*Assistant Examiner*—Amy E Pulliam
(74) *Attorney, Agent, or Firm*—Evenson, McKeown, Edwards & Lenahan, P.L.L.C.

(57) ABSTRACT

A nasally administrable composition which contains physiologically active compounds such as insulin, calcitonin, prostaglandin (PG) derivatives, monoclonal antibodies or interleukin derivatives (IL), and is enhanced in the in vivo absorbability of the physiologically active compound when administered nasally. The compositions are prepared by mixing fine particulate of the physiologically active compound with fine particulate of carrier having a mean particle size from 15 μm to 300 μm, and particle surface area from 0.1 to 0.4 m$^2$/g, a which adhere to the mucous membrane of the nasal cavity, and HPC—H as absorption accelerator.

7 Claims, 3 Drawing Sheets

Plasma concentration-time curves of PGD$_2$ after nasally administration of 100ug/body (mean ± S.E)

- ■ CaCO$_3$ /HPC-H
- ● CaCO$_3$ /HPC-L/Avicel
- ▲ CaCO$_3$ / 3% PVP
- ○ Sofarcon

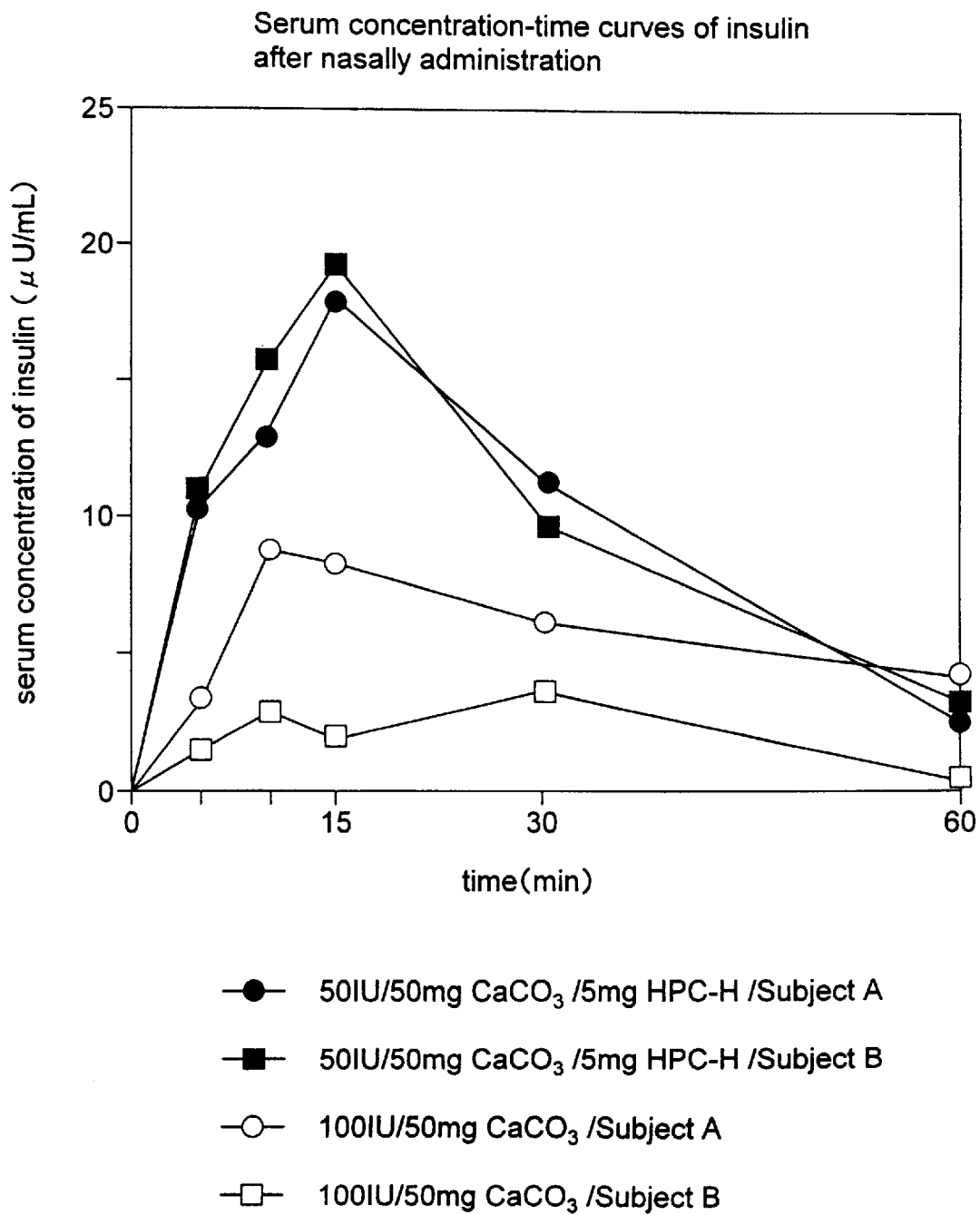

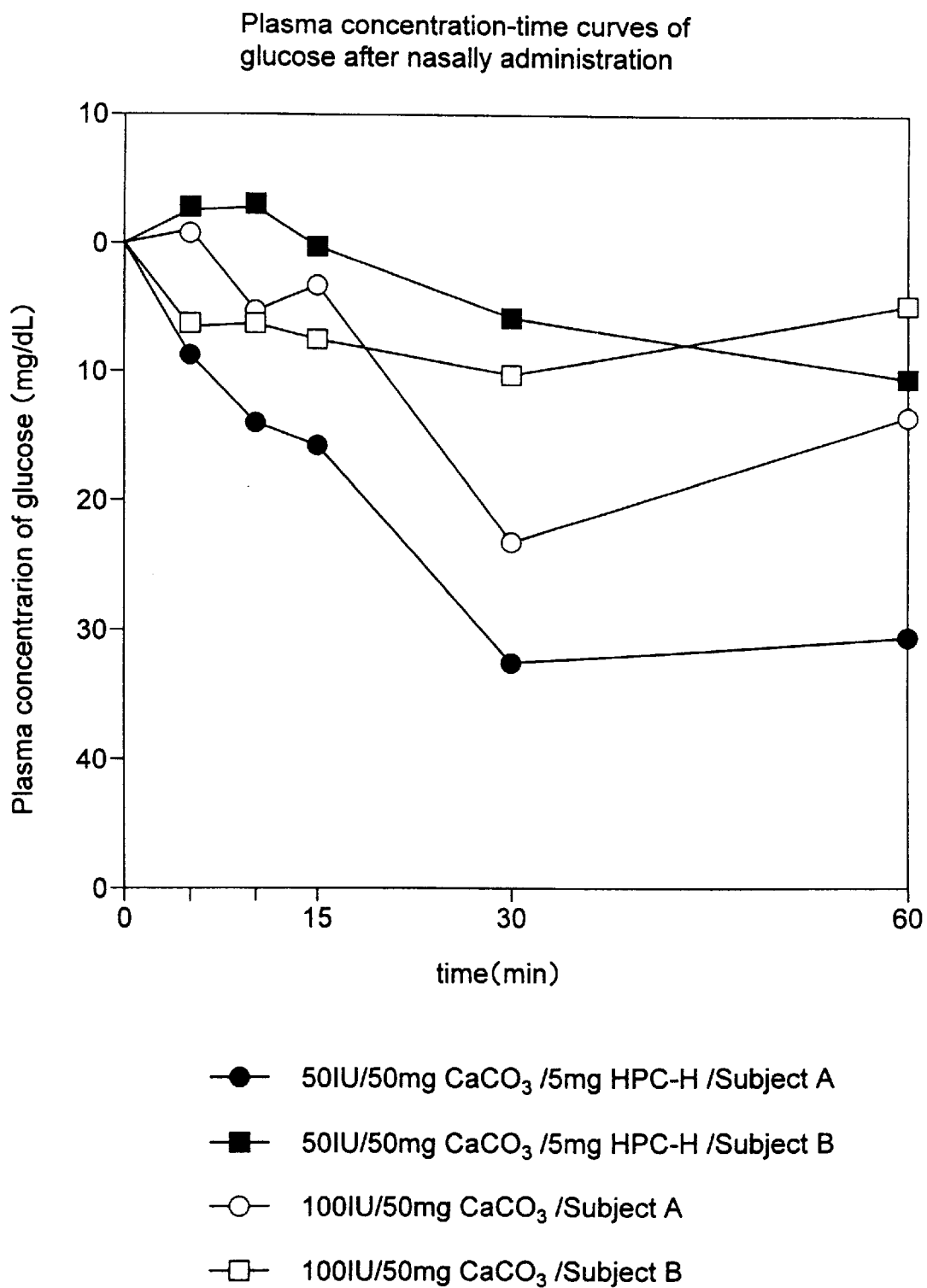

NASALLY ADMINISTRABLE COMPOSITIONS

BACKGROUND OF THE INVENTION

1. Field of the Invention

The present invention relates to a nasally administrable composition containing a physiologically active ingredient, and more particularly, to a nasally administrable composition containing a physiologically active compound with a mixture of unique carrier which adhere to the mucous membrane of the nasal cavity, and cellulose derivatives as absorption accelerator.

2. Description of the Prior Art

Hitherto, there have been developed nasally administrable preparations for physiologically active compounds unlikely to be administered orally. As one example of the preparations, an aerosol in the form of a suspension has been developed for nasal inhalation of calcitonin, in which a fluorinated hydrocarbon is used as a spouting agent. As another means for nasal administration of calcitonin, a liquid spray preparation has also been proposed. However, nasally administrable preparations so far proposed cannot be sufficient because of poor absorbability of physiologically active compounds or local irritability.

The inventor of the present invention has actively been studying a nasally administrable preparations of physiologically active peptides unlikely to be administered orally such as insulin, calcitonin. parathyroid hormone (PTH), human growth hormone (HGH) and so on. As a result of intensive studies, he has proposed nasally administrable composition using a unique carrier, wherein the physiologically active peptide is dispersed and absorbed homogeneously onto the carrier, and is highly absorbable into the body via nasal route.

Through further extensive studies and researches, the inventor of the present invention has found that the amounts of absorbed physiologically active compound into a body via nasal route well proportion to size of surface area of the carrier. Further, the inventor has found that the absorbability of the physiological peptide into a body via nasal route increase when the carrier adhere and stay on the mucous so membrane of the nasal cavity.

SUMMARY OF THE INVENTION

Accordingly, the object of the present invention is to provide a nasally administrable composition that can nasally administer physiologically active compound with higher bioavailability with less irritability than the preparations so far proposed using the carrier, wherein the carrier adhere to the mucous membrane of the nasal cavity.

One aspect of the present invention is to provide the nasally administrable composition comprising:

(a) an effective amount of physiologically active compound;

(b) fine particulate of carrier having a mean particle size from 15 $\mu$m to 300 $\mu$m, and particle surface area from 0.1 $m^2$/g to 0.4 $m^2$/g, which adhere to the mucous membrane of the nasal cavity; and (c) cellulose derivatives as absorption accelerator, wherein said physiologically active compound is dispersed homogeneously in and adsorbed homogeneously onto the mixture of said carrier and the cellulose derivatives.

In the specific embodiment of the present invention is the nasally administrable composition comprising:

(a) an effective amount of physiologically active compound selected from the group consisting of insulin, calcitonin and prostaglandin (PG) derivative;

(b) fine particulate of carrier having a mean particle size from 15 $\mu$m to 300 $\mu$m, and particle surface area from 0.1 $m^2$/g to 0.4 $m^2$/g, which adhere to the mucous membrane of the nasal cavity; and (c) high substituted hydroxypropylcellulose having 53.4% to a 77.5% of hydroxypropyl group in the compound (HPC—H) as absorption accelerator, wherein said physiologically active compound is dispersed homogeneously in and adsorbed homogeneously onto the mixture of said carrier and HPC—H.

In still another specific embodiment of the present invention is the composition in which HPC—H is contained at a rate of from 5.0% to 70.0%, per the loot total weight of the composition.

The other aspect of the present invention is to provide a mixed carrier to be used for nasally administrable composition comprising:

(a) fine particulate of aluminum compound, calcium compound or magnesium compound having a mean particle size from 15 $\mu$m to 300 $\mu$m, and particle surface area from 0.1 $m^2$/g to 0.4 $m^2$/g, which adhere to the mucous membrane of the nasal cavity, and (b) high substituted hydroxypropylcellulose having 53.4% to 77.5% of hydroxypropyl group in the compound (HPC—H).

In still another aspect of the present invention, use of high substituted hydroxypropylcellulose having 53.4% to 77.5% of hydroxypropyl group in the compound (HPC—H) as absorption accelerator for nasally administrable composition containing physiologically active compound such as insulin, calcitonin, prostaglandin (PG) derivatives, monoclonal antibodies, interleukin derivatives (IL) and so on, is provided.

BRIEF DESCRIPTION OF DRAWINGS

FIG. 2 is a graph showing a change of serum insulin level with time passage after administration of the composition of the present invention to two healthy male adults.

FIG. 3 is a graph showing a change of plasma glucose level with time passage after administration of the composition of the present invention to two healthy male adults.

DETAILED DESCRIPTION OF THE INVENTION

Figure 1:
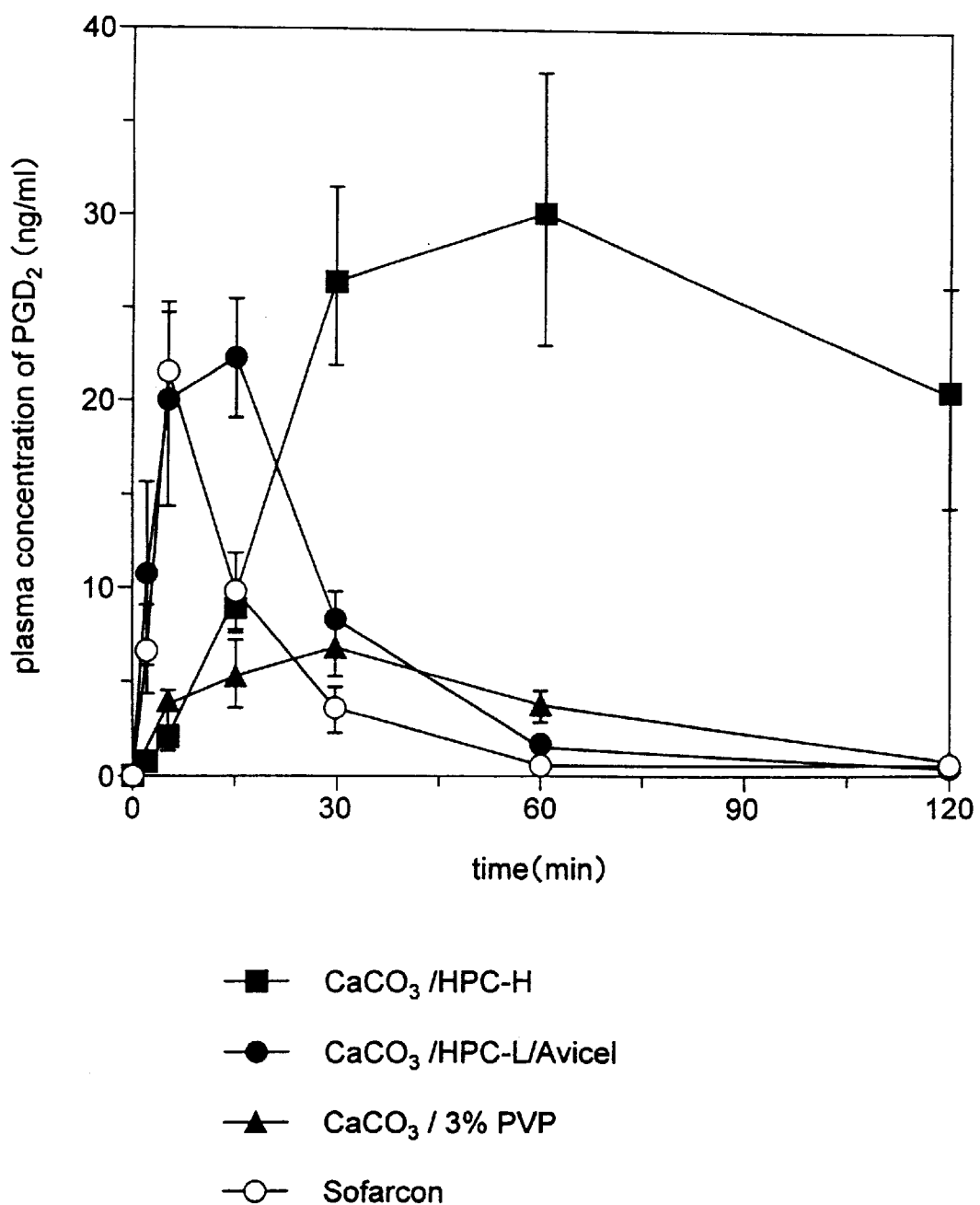
FIG. 1 is a graph showing a change of mean plasma PGD2 level h.3 with time passage after administration of the composition of SKY the present invention to five cynomolgus monkeys.

The carrier of the present invention is characterized by homogeneous dispersion to interior of the nasal cavity, adhesion to the mucous membrane of the nasal cavity without inhalation to the lung, and the sustainable adhesion of the carrier on the mucous membrane by its own weight and particle size.

Such a carrier to be used in the present invention may be fine particulate of aluminum compound, calcium compound or magnesium compound having a specific gravity of not more than 1.0 g/$cm^3$, a mean particle size from 15 $\mu$m to 300 $\mu$m, and a particle surface area from 0.1 $m^2$/g to 0.4 $m^2$/g.

The aluminum compound to be used as a carrier of the present invention may be, for example, aluminum hydroxy gel, aluminum hydroxychloride, synthetic aluminum silicate or colloidal aluminum silicate hydrate. The calcium compound may be, for example, calcium carbonate, calcium stearate, calcium chloride or calcium hydroxide. Furthermore, the magnesium compound may be, for example, magnesium carbonate, magnesium stearate or magnesium chloride. Among them, calcium carbonate is preferably used.

The carrier to be used in this invention has many pores on the surf ace as a result of granulation or re-granulation with carriers with each other.

The cellulose derivatives to be used as absorption accelerator of the present invention may be, for example, crystalline cellulose, methylcellulose, ethylcellulose, carboxymethylcellulose, hydroxyethylcellulose, hydroxypropylcellulose, or hydroxypropylmethylcellulose. Among them, high substituted hydroxypropylcellulose having 53.4% to 77.5% of hydroxypropyl group in the compound (HPC—H) is preferably used.

The cellulose derivatives to be used as absorption accelerator of the present composition may contain at a rate from 5.0% to 70.0%, per the 100% total weight of the composition.

The physiologically active compounds to be administered in the present composition are not particularly limited and may preferably be the compounds unlikely to be administered orally.

Examples of such physiologically active compounds include peptides, hypnotic and sedatives, anti-epileptics, minor tranquilizers, major tranquilizers, antidepressants, muscle relaxants, anti-allergic agents, antirheumatics, cardiotonics, antiarrthymics, antihypertensive diuretics, α-blocking agents, β-blocking agents, calcium channel antagonists, angiotensin converting enzyme inhibitors (AEC), antihypertensives, vitamins, coronary vasodilators, cerebral circulation and metabolism ameliorators, anti-arteriosclerotcs, cardiovascular agents, bronchodilators, anti-ucceratives, antiemetics, antiobesity agents, platelet aggregation inhibitors, antidiabetics/symptomatic anti-diabetics, and so on.

Among those physiologically active compounds, peptides such as insulin, calcitonin; prostaglandin (PG) derivatives such as $PGE_1$, $PGD_1$, $PGD_2$, $PGI_2$; monoclonal antibodies or interleukin derivatives such as IL - 1to IL -12; as well as biagura are preferred. These compounds are preferred to mix with the mixed carrier of the present invention in the form of fine particulate.

Therefore, a preferable mode of the present invention is a nasally administrable composition having fine particulate of PG, especially $PGD_2$ or insulin dispersed and adsorbed homogeneously onto the unique mixed carrier of calcium carbonate and HPC—H, wherein fine particulate of calcium carbonate have a mean particle size from 15 $\mu$m to 300 $\mu$m, and a particle surf ace area from 0.1 $m^2$/g to 0.4 $m^2$/g, and adhere to the mucous membrane of the nasal cavity.

The amount of the above-mentioned physiologically active compounds to be contained in the composition of the present invention is not specifically limited and may vary with the individual active ingredient to be chosen, the disease to be treated, desired number of administration, desired effect of therapy, and so on. Thus, when administering the composition of the present invention via the nasal route, the amount of the physiologically active compound to be administered can be determined on the basis of a comparison with other known preparation containing the same, in terms of bioavailability. Therefore, when preparing the composition of the present invention, it is appropriate to have the physiologically active compound contained at a rate from 0.0001% to 30%, preferably from 0.01% to 20%, more preferably from 0.1% to 5.0%, per the 100% total weight of the composition.

The composition of the present invention is prepared by admixing the physiologically active compound with the carrier and cellulose derivative, especially HPC—H, thereby yielding fine powder of a nasally administrable composition on which the physiologically active compound homogeneously adsorbed.

The composition of the present invention may further contain which increases the bloodstream and endogenous PG level Examples of such absorption enhancer include limaprost alfadex, beraprost sodium, kallikrein, isositol hexanicotinate, isosltol hexanicotinate/pyrldoxal calcium phosphate, tocopherol nicotinate, nicomol, niceritrol, hepronicate, cyclandelate, cinnarizine, and so on. The composition of the present invention may also contain the other conventional excipients such as fillers, stabilizers, binders, lubricants and the like those used in this technical fields.

In order to prevent the activity loss of the physiologically active compound prior to administration, it may be filled in low-grease type capsules and packaged in an appropriate form, preferably in a closed form, such as combined blister and aluminum packaging.

The following Test Examples show the specific effects offered by the compositions of the present invention.

Test Example 1

Preparation of the composition of the present invention $PGD_2$ was selected as the physiologically active compound; calcium carbonate was selected as the carrier, and hydroxypropylcellulose (HPC) was selected as the absorption accelerator to prepare the composition.

These ingredients were admixed to make the composition of the present invention containing $PGD_2$ at 100 ug/50 mg of calcium carbonate/50 mg of HPC/capsule, and the resultant mixture was filled into capsules.

The absorption accelerators were HPC having 53.4% to 77.5% of hydroxypropoxy group in the compound (HPC—H), and mixture of HPC having 5.0% to 16.0% of hydroxypropoxy group in the compound (HPC—L) and crystalline cellulose AVICEL®.

As the comparative examples, the mixed carrier of calcium carbonate with 0.3% polyvinylpyrolidone (PVP), and sofarcon were used as the comparative carriers previously proposed by the present inventor.

The mean particle size of each carriers were from 45 $\mu$m to 50 $\mu$m.

Absorption after nasal administration

The composition (amount of administration: 100 ug/ 100 mg/body) was nasally administered to five cynomolgus monkeys weighting approximately 5 kg, and blood sample was collected from each subject at 0, 1, 5, 15, 30, 60 and 120 minutes after administration. The concentration of $PGD_2$ in each blood sample was assayed with conventional HPLC method.

The results are shown in FIG. 1, as a change of mean plasma $PGD_2$ level with time passage after administration of the composition of the present invention to five cynomolgus monkeys.

As is apparent from FIG. 1, the composition of the present invention using HPC, especially HPC—H, as the carrier attained a high degree of absorption of $PGD_2$ into the blood through nasal route.

The ratio of bioavailability against intravenous injection is summarized in Table 1 below.

TABLE 1

| Carrier/<br>Accelerator | Ratio of bioavailability<br>against i.v. route |
|---|---|
| $CaCO_3$/HPC-H | 68.2% |
| $CaCO_3$/HPC-L/Avicel | 18.4% |
| $CaCO_3$/3% PVP | 11.5% |
| Sofarcon | 11.4% |

As is apparent from Table 1 above, the composition of the present invention attained high degree of absorption of $PGD_2$ into the body via nasal route, and the bioavailability of the present invention's composition using HPC—H as the absorption accelerator is approximately 70% against the bioavailability of the intravenously injection. This result shows the extreme usefulness of the composition of the present invention. Furthermore, the bioavailability of other composition of the sent invention using HPC—L as the absorption accelerator, is higher than that of the comparative examples, and these datum show significant usefulness of the nasal administration of the physiologically active compounds unlikely to be administered orally.

Test Example 2

Preparation of the composition of the present invention

Insulin was selected as the physiologically active compound, calcium carbonate was selected as the carrier, and HPC—H was selected as the absorption accelerator to prepare the composition.

These ingredients were admixed to make the composition of the present invention containing insulin 50 IU/50 mg of calcium carbonate/5 mg of HPC—H/capsule, and the resultant mixture was filled into capsules.

As the comparative examples, the composition containing insulin 100 IU/50 mg of calcium carbonate/capsule was used.

The mean particle size of each carriers were from 20 μm to 45 μm.

Absorption after nasal administration

The resultant composition was nasally administered once at a dose of 50 mg to two healthy male adults and blood sample (2.5 ml) was collected from each subject at 0, 1, 5, 15, 30 and 60 minutes after the administration. The concentration of insulin in each blood sample was assayed and simultaneously the average in fall of the blood glucose was measured.

The results are shown in FIG. 2 and FIG. 3.

FIG. 2 is a graph showing a change of serum insulin level with time passage, and FIG. 3 is a graph showing a change of plasma glucose level with time passage after administration of the composition of the present invention.

As is apparent from those figures, the composition of the present invention containing 50 IU of insulin and using HPC—H as the absorption accelerator attained a high degree of absorption of insulin into the blood through nasal route compare with the comparative composition in which 100 IU of insulin contained.

The following are the examples of the composition according to the present invention, which, however, are non-limiting.

Powdery composition for nasal administration 1

A $PGD_2$ composition was prepared from the following ingredients:

| $PGD_2$ | 5 g |
|---|---|
| Calcium carbonate | 50 g |
| HPC-H | 45 g |
| | 100 g |

Each 100mg of fine powder comprising the above-mentioned ingredients were filled into capsules for nasal administration.

Powdery composition for nasal administration 2

An IL-2 (genetical recombination) composition was prepared from the following ingredients:

| IL-2 | 0.6 million units |
|---|---|
| Calcium carbonate | 50 mg |
| HPC-H | 50 mg |

A fine powder comprising the above-mentioned ingredients was filled into capsule for nasal administration.

Powdery composition for nasal administration 3

An insulin composition was prepared from the following ingredients:

| Insulin | 50 units |
|---|---|
| Calcium carbonate | 50 mg |
| HPC-H | 10 mg |

A fine powder comprising the above-mentioned ingredients was filled into capsule for nasal administration.

What is claimed is:

1. A nasally administrable composition, comprising an effective amount of a physiologically active compound; and a mixture of:
   (A) a fine particulate carrier having a mean particle size from 15 μm to 300 μm and a particle surface area from $0.1m^2/g$ to $0.4m^2/g$, and which is capable of adhering to the mucous membrane of the nasal cavity; and
   (B) a highly substituted hydroxypropylcellulose having 53.4% to 77.5% hydroxypropyl groups as an absorption accelerator,
   wherein said physiologically active compound is dispersed homogeneously in and adsorbed onto the mixture of said carrier and said highly substituted hydroxypropylcellulose.

2. The nasally administrable composition of claim 1, wherein said highly substituted hydroxypropylcellulose is present in an amount of from 5.0% to 70.0% per total composition weight.

3. The nasally administrable composition of claim 1, further comprising an absorption enhancer.

4. The nasally administrable composition of claim 3, wherein the absorption enhancer is selected from the group consisting of limaprost alfadex, beraprost sodium, kallikrein, isositol hexanicotinate, isositol hexanicotinate/pyridoxal calcium phosphate, tocopherol nicotinate, nicomol, niceritrol, hepronicate, cyclandelate, cinnarizine and a mixture thereof.

5. A method of increasing an amount of absorption of a physiologically active compound of a nasally administrable composition, comprising
  mixing together a highly substituted hydroxypropylcellulose having 53.4% to 77.5% hydroxypropyl groups as an absorption accelerator with a fine particulate carrier having a mean particle size from 15 μm to 300 μm and a particle surface area from $0.1m^2/g$ to $0.4m^2/g$, which is capable of adhering to the mucous membrane of the nasal cavity; and dispersing homogeneously in and adsorbing onto the mixture of said carrier and said highly substituted hydroxypropylcellulose, said physiologically active compound.

6. A nasal administrable composition, comprising an effective amount of a physiologically active compound; and a mixture of:
  (A) a fine particulate of calcium carbonate having a mean particle size from 15 μm to 300 μm and a particle surface area from $0.1m^2/g$ to $0.4m^2/g$, and which is capable of adhering to the mucous membrane of the nasal cavity; and
  (B) a highly substituted hydroxypropylcellulose having 5.3% to 77.5% hydroxypropyl groups in the compound.

7. The nasally administrable composition of claim 6, wherein the highly substituted hydroxypropylcellulose is present in an amount of from 5.0% to 70.0%, per the total weight of said mixed carrier.

* * * * *